United States Patent
Greaves et al.

(10) Patent No.: US 10,940,102 B2
(45) Date of Patent: Mar. 9, 2021

(54) PROCESS FOR PROTECTING AND REPAIRING KERATIN FIBRES, BASED ON OXIDIZED POLYSACCHARIDE AND ON (POLY)SACCHARIDE WITH AMINE GROUP

(71) Applicant: L'OREAL, Paris (FR)

(72) Inventors: Andrew Greaves, Magny-le-Hongre (FR); Nawel Baghdadli, Massy (FR); Lucien Bildstein, Aulnay-sous-Bois (FR); Berangere Baril, Suresnes (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/557,304

(22) PCT Filed: Mar. 14, 2016

(86) PCT No.: PCT/EP2016/055435
§ 371 (c)(1),
(2) Date: Sep. 11, 2017

(87) PCT Pub. No.: WO2016/142551
PCT Pub. Date: Sep. 15, 2016

(65) Prior Publication Data
US 2018/0049964 A1    Feb. 22, 2018

(30) Foreign Application Priority Data
Mar. 12, 2015  (FR) ..................... 1552066

(51) Int. Cl.
| | | |
|---|---|---|
| *A61K 8/73* | (2006.01) | |
| *A61K 8/60* | (2006.01) | |
| *A61Q 5/12* | (2006.01) | |
| *A61Q 5/00* | (2006.01) | |

(52) U.S. Cl.
CPC ............. *A61K 8/73* (2013.01); *A61K 8/60* (2013.01); *A61K 8/736* (2013.01); *A61Q 5/00* (2013.01); *A61Q 5/12* (2013.01); *A61K 2800/87* (2013.01)

(58) Field of Classification Search
None
See application file for complete search history.

(56) References Cited

U.S. PATENT DOCUMENTS

| | | |
|---|---|---|
| 5,046,516 A | 9/1991 | Barradas |
| 5,957,140 A | 9/1999 | McGee |
| 2002/0172653 A1 | 11/2002 | Cannell et al. |
| 2002/0193264 A1 | 12/2002 | Cannell et al. |
| 2003/0053977 A1 | 3/2003 | Cannell et al. |
| 2008/0063617 A1 | 3/2008 | Abrahams et al. |
| 2009/0270346 A1 | 10/2009 | Tijsma et al. |

FOREIGN PATENT DOCUMENTS

| | | |
|---|---|---|
| EP | 0002506 A1 | 6/1979 |
| FR | 2842200 A1 | 1/2004 |
| FR | 2854161 A1 | 10/2004 |
| FR | 2944967 A1 | 11/2010 |
| FR | 2987742 A1 | 9/2013 |
| WO | 2013/132062 A1 | 9/2013 |

OTHER PUBLICATIONS

AMS, ([retrieved from on-line website: https://www.ams.usda.gov/sites/default/files/media/Chitosan%20TR.pdf, published in 2004. pp. 1-8]). (Year: 2004).*

FR2944967—EPO English translation ([retrieved from on-line website: http://translationportal.epo.org/emtp/translate/?ACTION=description-retrieval&COUNTRY=FR&ENGINE=google&FORMAT=docdb&KIND=A1&LOCALE=en EP&NUMBER=2944967&OPS=ops.epo.org/3.2&SRCLANG=fr&TRGLANG=en)], last visit Feb. 14, 2020 (Year: 2009).*

International Search Report for counterpart PCT/EP2016/055435, dated May 9, 2016.

Fredon, E., et al., "Hydrophobic films from maize bran hemicelluloses," Carbohydrate Polymers, vol. 49, No. 1, Jul. 1, 2002, pp. 1-12.

Onsoyen E., et al., "Adding Benefits to Cosmetic Formulations by Tailormade Chitosans," SOFW Journal, vol. 117, No. 16, Oct. 24, 1991, pp. 633-637.

Wing, R.E., et al., "Water soluble oxidized starches by peroxide reactive extrusion," Industrial Crops and Products, 7, 1997, pp. 45-52.

* cited by examiner

*Primary Examiner* — Kyung S Chang
(74) *Attorney, Agent, or Firm* — The Marbury Law Group, PLLC

(57) ABSTRACT

The invention relates to i) a process for treating keratin fibres, in particular human keratin fibres such as the hair, employing a) at least one oxidized polysaccharide, in particular oxidized inulin, and b) at least one (poly)saccharide with amine group(s); ii) a composition comprising the ingredients a) and b); iii) the use of a) and b) to treat keratin fibres, in particular human keratin fibres such as the hair, and iv) a multi-compartment kit or device comprising a) and b). The invention makes it possible to obtain good hair-conditioning cosmetic properties, with a long-lasting effect.

9 Claims, No Drawings

PROCESS FOR PROTECTING AND REPAIRING KERATIN FIBRES, BASED ON OXIDIZED POLYSACCHARIDE AND ON (POLY)SACCHARIDE WITH AMINE GROUP

CROSS REFERENCE TO RELATED APPLICATIONS

This is a national stage application of PCT/EP2016/055435, filed internationally on Mar. 14, 2016, which claims priority to French Application No. 1552066, filed on Mar. 12, 2015, both of which are incorporated by reference herein in their entireties.

The invention relates to i) a process for treating keratin fibres, in particular human keratin fibres such as the hair, employing a) at least one oxidized polysaccharide, in particular oxidized inulin, and b) at least one (poly)saccharide with amine group(s); ii) a composition comprising the ingredients a) and b); iii) the use of a) and b) to treat keratin fibres, in particular human keratin fibres such as the hair, and iv) a multi-compartment kit or device comprising a) and b).

Hair is generally damaged and weakened by the action of external atmospheric agents such as light, sun and bad weather, and also by mechanical or chemical treatments, such as brushing, combing, dyeing, bleaching, permanent-waving, relaxing and repeated washing. Hair is thus damaged by these various factors and may in the long run become dry, coarse, brittle or dull or split or limp.

Thus, to overcome these drawbacks, it is common practice to resort to hair treatments which make use of compositions intended for conditioning the hair appropriately by giving it satisfactory cosmetic properties, especially smoothness, sheen, a soft feel (a natural feel; the hair is no longer coarse), suppleness, a lightweight feel, good disentangling properties leading to easy combing, and good manageability of the hair which is thus easy to shape.

These haircare compositions may be, for example, conditioning shampoos, hair conditioners, masks or serums. However, the conditioning effect obtained fades out in the course of successive shampoo washes and does not show satisfactory persistence on shampooing.

It is known practice to employ care compositions comprising reducing sugars such as monosaccharides, used as conditioning agents, especially to repair keratin fibres which have been damaged by harsh treatments.

Indeed, patent application US 2002/0193264 describes a process for conditioning keratin fibres, in which at least one sugar chosen from monosaccharides is applied to said fibres, and a step of heating the keratin fibres is carried out. Similarly, patent application US 2002/0172653 discloses a process for conditioning keratin fibres comprising a step of applying to said fibres a sugar chosen from specific $C_5$-$C_7$ monosaccharides and a step of heating the keratin fibres. However, the use of reducing sugars followed by a heat treatment may lead to an undesired modification of the colour of the keratin fibres. Furthermore, reducing sugars degrade easily, especially under the action of shampoos, which results in the cosmetic properties conferred on the fibres not persisting. Thus, the keratin fibres are not protected, repaired or cosmetically transformed in a long-lasting manner.

In the field of dyeing, patent application FR 2 944 967 discloses the use of oxidized polysaccharides for protecting the colour of keratin fibres that have been artificially dyed. International application WO 2013/132062 also discloses a process for treating the hair, which consists in using one or more oxidized polysaccharides and in raising the temperature of the keratin fibres. Moreover, patent application US 2003/0053977 describes a process for protecting keratin fibres which uses heat and a glucosamine. Nonetheless, the results obtained are not always satisfactory in terms of repair, protection or conditioning of the keratin fibres, in particular damaged and/or sensitized hair, especially in terms of softness of the surfaces of said fibres, in particular at the dry ends, or are not always satisfactory for disentangling wet keratin fibres.

There is therefore a real need to develop a composition and a process for treating keratin fibres such as the hair, which is able to condition and/or protect the hair in a long-lasting manner, without leading to a modification of its colour. It is also advantageous to find a means for treating damaged keratin fibres by repairing them, that is to say by intrinsically improving the cosmetics of the keratin fibres, reducing breakage of the keratin fibres and/or preventing breakage of the keratin fibres.

This (these) technical problem(s) has (have) been solved by the process for treating keratin fibres, especially human keratin fibres, in particular the hair, comprising:
(i) a step consisting in applying, to said fibres, a) one or more, preferably nonionic or anionic, oxidized polysaccharide(s);
(ii) a step consisting in applying, to said fibres, b) one or more (poly)saccharide(s) with amine group(s);
it being understood that steps (i) and (ii) may be carried out simultaneously or sequentially, and preferably steps (i) and (ii) are carried out simultaneously.

Another subject of the invention is a composition comprising:
a) one or more, preferably nonionic or anionic, oxidized polysaccharide(s); and
b) one or more (poly)saccharide(s) with amine group(s).

Another subject of the invention is the use of ingredients a) and b) to improve the conditioning of keratin fibres and/or to repair damaged keratin fibres and/or to prevent breakage of keratin fibres.

In particular, hair treated via the process according to the invention remains well-behaved since no presence of frizziness is observed. Thus, the hairs are aligned, smooth and disentangle easily, which makes them easier to comb. The treated hair also has more body (it is not limp) and is thus easier to style. The treated hair shapes well. Moreover, the treated hair is also shinier and feels softer. It is stronger and less brittle.

After treatment, the hair is not laden, and has a natural feel.

The process according to the invention has the advantage of giving good persistence of these good hair-conditioning cosmetic properties after shampooing. Thus, the treated hair is conditioned in a long-lasting manner.

In the following text, unless indicated otherwise:
"organic or inorganic acid salt" is understood more particularly to mean the salts chosen from a salt derived from i) hydrochloric acid HCl, ii) hydrobromic acid HBr, iii) sulfuric acid $H_2SO_4$, iv) alkylsulfonic acids: Alk-S(O)$_2$OH, such as methylsulfonic acid and ethylsulfonic acid; v) arylsulfonic acids: Ar—S(O)$_2$OH such as benzenesulfonic acid and toluenesulfonic acid; vi) citric acid; vii) succinic acid; viii) tartaric acid; ix) lactic acid; x) alkoxysulfinic acids: Alk-O—S(O)OH such as methoxysulfinic acid and ethoxysulfinic acid; xi) aryloxysulfinic acids such as tolueneoxysulfinic acid and phenoxysulfinic acid; xii) phosphoric acid $H_3PO_4$; xiii) acetic acid $CH_3C(O)OH$; xiv) triflic acid $CF_3SO_3H$; and xv) tetrafluoroboric acid $HBF_4$;

moreover, the addition salts that may be used in the context of the invention are especially chosen from addition salts with a cosmetically acceptable base such as basifying agents as defined below, for instance alkali metal hydroxides, such as sodium hydroxide or potassium hydroxide, aqueous ammonia, amines or alkanolamines;

the expression "at least one" is equivalent to "one or more"; and the expression "inclusive" for a range of concentrations means that the limits of the range are included in the defined range.

a) Oxidized Polysaccharides.

According to a particular embodiment of the invention, the oxidized polysaccharide(s) is (are) chosen from anionic and nonionic polysaccharides.

"Polysaccharides" is understood to mean glycans, polyglycosides, polysaccharides or complex carbohydrates, which are polymers constituted of several monosaccharides bonded together by O-glycosidic bonds. They are more particularly polymers formed from a certain number of monosaccharides having the general formula: —[$C_x(H_2O)_y$)]$_n$— where x is an integer greater than or equal to 5, preferably x is greater than or equal to 6, in particular x is between 5 and 7 inclusive and preferably x=6, and y is an integer which represents x−1, and n is an integer greater than or equal to 2, particularly of between 3 and 1000 inclusive, more particularly between 5 and 500 and preferentially between 10 and 200.

The anionic or nonionic oxidized polysaccharides are constituted of monosaccharide units that may comprise five or more carbon atoms, preferably six or more carbon atoms, and more particularly six carbon atoms.

The nonionic or anionic oxidized polysaccharides comprise one or more aldehydes and optionally one or more anionic groups.

These anionic groups are preferably carboxyl or carboxylate groups.

The anionic or nonionic oxidized polysaccharides according to the invention may be represented by formula (I) below:

$$P\text{—}(CHO)_m(COOX)_n \qquad (I)$$

in which formula (I):

P represents a polysaccharide chain constituted of monosaccharides comprising 5 carbon atoms or more than 5 carbon atoms, preferably 6 or more than 6 carbon atoms and more particularly 6 carbon atoms;

X is chosen from a hydrogen atom, the ions derived from an alkali metal or an alkaline-earth metal such as sodium or potassium, aqueous ammonia, organic amines such as monoethanolamine, diethanolamine, triethanolamine and 3-amino-1,2-propanediol and basic amino acids such as lysine, arginine, sarcosine, ornithine and citrulline;

m+n is greater than or equal to 1;

m is such that the degree of substitution of the polysaccharide with one or more aldehyde groups (DS(CHO)) is within the range from 0.001 to 2 and preferably from 0.005 to 1.5;

n is such that the degree of substitution of the polysaccharide with one or more carboxylic groups (DS(COOX)) is within the range from 0 to 2 and preferably from 0.001 to 1.5.

The term "degree of substitution DS(CHO) or DS(COOX) of the polysaccharides according to the invention" is understood to mean the ratio between the number of carbons oxidized to give an aldehyde or carboxylic group for all the repeating units and the number of elemental monosaccharides (even opened by preoxidation) constituting the polysaccharide.

The groups CHO and COOX may be obtained during the oxidation of certain carbon atoms, for example in position C2, C3 or C6, of a saccharide unit comprising 6 carbon atoms. Preferably, the oxidation may take place at C2 and at C3, more particularly from 0.01% to 75% by number and preferably from 0.1% to 50% by number of the rings having possibly been opened.

The polysaccharide chain, represented by P, is preferably chosen from inulins, celluloses, starches, guar gums, xanthan gums, pullulan gums, alginate gums, agar-agar gums, carrageenan gums, gellan gums, gum arabics, xyloses and tragacanth gums, and derivatives thereof, cellobiose, maltodextrin, scleroglucan, chitosan, ulvan, fucoidan, alginate, pectin, heparin and hyaluronic acid, or mixtures thereof.

More preferentially, the polysaccharide chain is chosen from inulins and starches.

Even more preferentially, the polysaccharide chain is inulin.

The term "derivative" is understood to mean the compounds obtained by chemical modification of the mentioned compounds. They may be esters, amides or ethers of said compounds.

The oxidation may take place according to a process known in the art, for example according to the process described in FR 2 842 200, in document FR 2 854 161 or in the article "Hydrophobic films from maize bran hemicelluloses" by E. Fredon et al., Carbohydrate Polymers 49, 2002, pages 1 to 12. Another oxidation process is described in the article "*Water soluble oxidized starches by peroxide reaction extrusion*", Industrial Crops and Products 75 (1997) 45-52— R. E. Wing, J. L. Willet. These oxidation processes are easy to perform, are efficient and do not generate any toxic by-products or by-products that are difficult to remove.

The peroxides that may be used in these oxidation processes may be an alkali metal or alkaline-earth metal percarbonate or perborate, an alkyl peroxide, peracetic acid or hydrogen peroxide. Hydrogen peroxide is particularly preferred, in so far as it is readily accessible and does not produce interfering by-products.

The amount of peroxide in the reaction medium is between 0.05 and 1 molar equivalent per glucose unit of the polysaccharide, preferably between 0.1 and 0.8 molar equivalent. It is preferable to add the peroxide in successive portions, leaving the reaction medium stirring between two additions.

A single phthalocyanin or a mixture of phthalocyanins, for example a mixture of cobalt phthalocyanin and of iron phthalocyanin, may be used as catalyst in the oxidation process. The amount of catalyst depends on the desired degree of substitution. In general, a small amount, for example an amount corresponding to 0.003 to 0.016 molar equivalent per 100 glucose units of polysaccharide, is suitable.

The process may also be carried out by placing the polysaccharide in pulverulent form in contact with the catalyst dissolved in a small volume of water and with the peroxide. This process is referred to as a "semi-dry" process.

The process may be carried out by reactive extrusion in the presence of peroxide.

More preferentially, the polysaccharide is obtained by oxidation of inulin, cellulose, carboxymethylcellulose, hydroxyethylcellulose, hydroxypropylcellulose, hydroxypropylmethylcellulose, methylcellulose, starch, starch acetate, hydroxyethyl starch, hydroxypropyl starch, guar gum, carboxymethyl guar gum, carboxymethylhydroxypropylguar gum, hydroxyethyl guar gum, hydroxypropyl guar gum, xylose or xanthan gum, carrageenan gum, cellobiose, maltodextrin, scleroglucan, chitosan, ulvan, fucoidan, alginate, pectin, heparin and hyaluronic acid, or mixtures thereof.

Preferentially, the polysaccharide is obtained by oxidation of inulin or starch, more preferentially by oxidation of inulin.

Preferentially, the polysaccharide is obtained by oxidation of inulin.

According to one embodiment, the polysaccharide is obtained by oxidation of inulin by performing a reactive extrusion process in the presence of hydrogen peroxide.

The polysaccharide chain before and after oxidation preferably has a weight-average molecular mass ranging from 400 to 15 000 000, better still from 500 to 10 000 000 and more particularly from 500 to 50 000 g/mol.

The polysaccharides that are most particularly preferred in the invention are those corresponding to formula (I) in which: P represents a polymer chain derived from inulin or from starch, m is such that the degree of substitution of the polysaccharide with one or more aldehyde groups (DS (CHO)) is within the range from 0.005 to 2.5, n is such that the degree of substitution of the polysaccharide with one or more carboxylic groups (DS(COOX)) is within the range from 0.001 to 2.

Even more preferably, the radical P of formula (I) as defined above represents a polymer chain derived from inulin, m is such that the degree of substitution of the polysaccharide with one or more aldehyde groups (DS (CHO)) is within the range from 0.01 to 1 and n is such that the degree of substitution of the polysaccharide with one or more carboxylic groups (DS(COOX)) is within the range from 0.01 to 2.

Advantageously, the oxidized polysaccharide(s) as defined above is (are) in a content ranging from 0.05% to 15% by weight, preferably ranging from 0.1% to 10% by weight and more preferentially ranging from 0.2% to 6% by weight relative to the total weight of the composition.

b) (Poly)Saccharides with Amine Group(s) and (Poly) Glucosamines

The second ingredient used in the present invention is b) one or more (poly)saccharide(s) with amino group(s).

The term "(poly)saccharide" is understood to mean:
i) monosaccharides comprising more than 5 carbon atoms of formula $C_x(H_2O)_x$, where x is an integer greater than or equal to 5, preferably x is greater than or equal to 6, in particular x is between 5 and 7 inclusive and preferably x=6;
ii) the polysaccharides as defined above, in particular the polysaccharides are constituted of monosaccharide units comprising more than 5 carbon atoms, preferably 6 or more, and more particularly six carbon atoms; and
iii) mixtures thereof.

The term "with amino group(s)" is understood to mean that the monosaccharide or polysaccharide is substituted with one or more amino group(s) $NR_1R_2$, i.e. at least one of the hydroxyl groups of the glycoside unit is replaced by an $NR_1R_2$ group, with $R_1$ and $R_2$, which are identical or different, representing i) a hydrogen atom, ii) a $(C_1-C_6)$alkyl group which is optionally substituted, preferably with one or more hydroxyl or $NH_2$ groups, iii) an aryl group such as phenyl, iv) an aryl($C_1-C_4$)alkyl group such as benzyl, v) a (hetero)cyclo($C_5-C_7$)alkyl group such as cyclohexyl, morpholinyl, piperazinyl or piperidinyl, vi) a (hetero)cyclo($C_5$-$C_7$)alkyl($C_1-C_4$)alkyl group such as cyclohexylmethyl, vii) —C(Y)—(Y')$_p$—R'$_1$, with Y and Y', which are identical or different, representing an oxygen or sulfur atom or N(R'$_2$), and preferably oxygen, p=0 or 1, preferably 0; and R'$_1$ and R'$_2$ representing i) to vi) from $R_1$ and $R_2$ defined above. Preferably, $R_1$ and $R_2$ represent a hydrogen atom.

According to one particular embodiment, the (poly)saccharides with amine group(s) of the invention are monosaccharides with amine group(s), preferentially glucopyrans with amine group(s), also referred to as glucosamine.

By way of examples, mention may be made of the $C_5$-$C_7$ monosaccharides substituted with one or more amino group(s), especially $C_5$ amino groups: the pentosamines. According to one particular embodiment of the invention, the pentosamines are chosen from the aldopentosamines and the ketopentosamines such as xylosamine, arabinosamine, lyxosamine, ribosamine, ribulosamine and xylulosamine.

By way of examples, mention may be made of the $C_5$-$C_7$ monosaccharides substituted with one or more amino group(s), especially $C_6$ amino groups: the hexosamines such as aldohexosamines and ketohexosamines. According to one embodiment of the invention, the hexosamines are chosen from glucosamine, allosamine, altrosamine, mannosamine, gulosamine, idosamine, galactosamine and talosamine. They are more particularly chosen from glucosamine and galactosamine.

By way of examples, mention may be made of the $C_5$-$C_7$ monosaccharides substituted with one or more amino group(s), especially $C_7$ amino groups:heptosamines such as aldoheptosamines and ketoheptosamines.

More preferentially, the (poly)saccharides with amine group(s) of the invention are glucosamines of formula (A) and the organic or inorganic acid salts or base salts thereof, and the solvates thereof such as the hydrates:

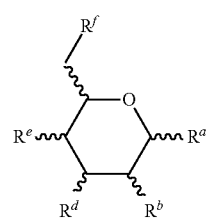

(A)

in which formula (A):
$R^a$, $R^b$, $R^d$, $R^e$ and $R^f$, which are identical or different, represent a hydroxyl or $(C_1-C_4)$alkoxy group, the alkyl group of which may be optionally substituted, especially with one or more hydroxyl or carboxyl groups, and an $NR_1R_2$ group, with $R_1$ and $R_2$ as defined above, in particular $R_1$ and $R_2$ are chosen from a hydrogen atom and —C(O)—R'$_1$ representing i) to vi) as defined above; preferably, $R_1$ and $R_2$ represent i) a hydrogen atom or ii) a $(C_1-C_6)$alkyl group such as methyl;
it being understood that at least one of the radicals $R^a$, $R^b$, $R^d$, $R^e$ and $R^f$ represents an $NR_1R_2$ group, preferably $R^b$ represents an $NR_1R_2$ group such as $NH_2$, and $R^a$, $R^d$, $R^e$ and $R^f$, represent a hydroxyl group.

Preferably, the compounds of formula (A) are of D configuration or otherwise referred to as D-glucopyran. The compounds of formula (A) are particularly of 1 (beta) anomeric configuration. According to one particular embodiment, the (poly)saccharides of the invention are chosen from the compounds of formula (A') below and the organic or inorganic acid salts or base salts thereof, and the solvates thereof such as the hydrates:

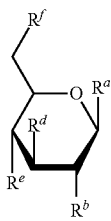

(A')

in which formula (A') $R^a$, $R^b$, $R^d$, $R^e$ and $R^f$ are as defined for (A) above.

According to another particular embodiment of the invention, the (poly)saccharides with amine group(s) of the invention are polysaccharides with amine group(s), of which the $C_5$-$C_7$ glycoside units, and the glycoproteins comprising $C_5$-$C_7$ glycoside units, comprise one or more amine groups.

More particularly, the (poly)saccharides with amine group(s) of the invention are polysaccharides with amine group(s); preferentially, the glycoside unit is glucopyranose with amine group(s), and these polysaccharide(s) with amine group(s) are then referred to as polyglucosamines.

According to one particular embodiment, the glycoside units of the polysaccharide with amine group(s) are of 1 (beta) anomeric configuration and/or D configuration.

According to one particular embodiment, the glycoside units of the polysaccharide with amine group(s) are joined to one another between the C1 carbon atoms of one glycoside unit and the C4 carbon atoms of the other glycoside unit, denoted (1→4), such as the polysaccharide with amine group(s) of formula (B) below and the organic or inorganic acid salts or base salts thereof, and the solvates thereof such as the hydrates:

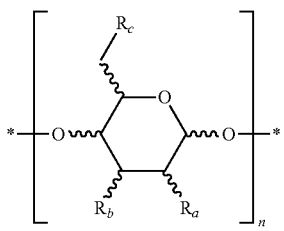

(B)

in which formula (B):
  n is an integer greater than or equal to 2, particularly between 3 and 1000 inclusive, and more particularly between 5 and 500, preferentially between 10 and 200;
  $R_a$, $R_b$, and $R_c$, which are identical or different, represent a hydroxyl or ($C_1$-$C_4$)alkoxy group, the alkyl group of which may be optionally substituted, especially with one or more hydroxyl or carboxyl groups, and an $NR_1R_2$ group, with $R_1$ and $R_2$ as defined above, in particular $R_1$ and $R_2$ are chosen from a hydrogen atom and —C(O)—$R'_1$ representing i) to vi) defined above; preferably, $R_1$ and $R_2$ represent i) a hydrogen atom or ii) a ($C_1$-$C_6$)alkyl group such as methyl;
it being understood that at least one of the radicals $R_a$, $R_b$, and $R_c$ represents an $NR_1R_2$ group; preferably, $R_a$ represents an $NR_1R_2$ group, and $R_b$ and $R_c$ represent a hydroxyl group.

More particularly, the polysaccharide(s) with amine group(s) of the invention is (are) of formula (B') below, and the organic or inorganic acid salts or base salts thereof, and the solvates thereof such as the hydrates:

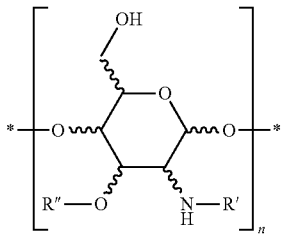

(B')

in which formula (B'):
  R' represents a hydrogen atom or a ($C_1$-$C_4$)alkylcarbonyl group such as acetyl;
  R" represents a hydrogen atom or a ($C_1$-$C_4$)alkyl group optionally substituted with a carboxyl group such as —CH($CO_2H$)—$CH_3$;
  n is as defined for (B); preferably it is an integer between 2 and 200 inclusive.

Preferably, the glycoside units of formula (B) or (B') are of D configuration or otherwise referred to as D-glucopyran. The units of formula (B) or (B') are particularly of 1 (beta) anomeric configuration. According to one particular embodiment, the (poly)saccharides of the invention are chosen from the compounds of the formula (B") below and the organic or inorganic acid salts or base salts thereof, and the solvates thereof such as the hydrates:

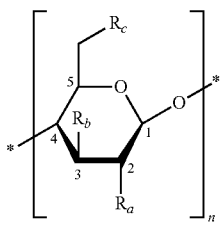

(B")

in which formula (B") $R_a$, $R_b$ and $R_c$ are as defined for (B) above and n represents an integer between 5 and 500 inclusive, particularly between 10 and 300 inclusive and preferentially between 15 and 100 inclusive.

Preferentially, the polysaccharide(s) with amine group(s) of the invention is (are) chosen from chitin and chitosan and their derivatives, preferably chitosan. They are more particularly chosen from those of formula (B''') below and the organic or inorganic acid salts thereof, and the solvates thereof such as the hydrates,

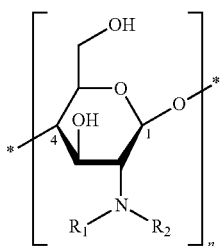

(B''')

in which formula (B'''):
  $R_1$ and $R_2$ are as defined in formulae (B), (B') or (B"); preferably, $R_1$ and $R_2$ represent a hydrogen atom; and n represents an integer between 5 and 500 inclusive; particularly between 10 and 300 inclusive and preferentially between 15 and 100 inclusive.

According to another particular embodiment, the (poly)saccharides with amine group(s) of the invention are a mixture of monosaccharides and polysaccharides as defined above.

According to another preferred embodiment, the (poly)saccharide(s) with amine group(s) of the invention is (are) present in the composition in an amount of between 0.01% and 10% by weight, more particularly of between 0.1% and 5% by weight relative to the total weight of the composition.

The Compositions

The Composition of the Invention

The composition(s) of the invention comprising ingredients a) and b) as defined above are cosmetic, i.e. contain a physiologically acceptable medium, that is to say that is compatible with human keratin materials such as the skin (of the body, face, around the eyes or the scalp), the hair, the eyelashes, the eyebrows, body hair, the nails or the lips.

The physiologically acceptable medium of the composition(s) used in the process according to the invention is advantageously an aqueous medium. It may be constituted, for example, of water or of a mixture of water and of at least one cosmetically acceptable organic solvent. Examples of organic solvents that may be mentioned include $C_2$-$C_4$ lower alcohols, such as ethanol and isopropanol; polyols, especially those having from 2 to 6 carbon atoms, for instance glycerol, propylene glycol, butylene glycol, pentylene glycol, hexylene glycol, dipropylene glycol or diethylene glycol; polyol ethers, for instance 2-butoxyethanol, propylene glycol monomethyl ether and diethylene glycol monomethyl ether or monoethyl ether; and mixtures thereof.

Preferably, the cosmetic composition(s) comprise from 50% to 99.5% by weight of water, relative to the weight of the composition(s).

The composition(s) used according to the invention may also contain one or more cosmetic additives chosen from nonionic, anionic, cationic and amphoteric surfactants, vitamins and provitamins, including panthenol, sunscreens, fillers, colorants, nacreous agents, opacifiers, sequestrants, film-forming polymers, plasticizers, thickeners, oils, antioxidants, antifoams, moisturizers, emollients, penetrants, fragrances and preserving agents.

The composition(s) used according to the invention may be in any galenical form conventionally used for application to the hair and especially in the form of aqueous solutions, aqueous-alcoholic solutions, oil-in-water (O/W), water-in-oil (W/O) or multiple (triple: W/O/W or O/W/O) emulsions, aqueous gels or aqueous-alcoholic gels. These compositions are prepared according to the usual methods. Preferably, the composition is in the form of an aqueous or aqueous-alcoholic solution or gel.

pH of the Composition(s):

According to one particular embodiment of the invention, the composition which comprises b) one or more monosaccharide(s) with amine group(s) as defined above, especially glucosamine, in particular of formula (A) or (A') as defined above, is at a pH of between 2.5 and 9.5 inclusive.

According to a preferred embodiment of the invention, the composition which comprises b) one or more polysaccharide(s) with amine group(s) as defined above, especially in particular of formula (B), (B'), (B'') or (B''') as defined above, such as chitosan, is at an acidic pH, in particular at a pH of between 1 and 6 inclusive, more particularly between 2 and 5, preferably between 3 and 4.

The pH values may be adjusted by an organic or inorganic acid, or by an alkaline agent chosen from inorganic or organic or hybrid alkaline agents or mixtures thereof.

The term "organic acid" is understood to mean an acid, i.e. a compound that is capable of releasing a cation or proton $H^+$ or $H_3O+$, in aqueous medium, which comprises at least one optionally unsaturated, linear or branched $C_1$-$C_{20}$ hydrocarbon-based chain, or a (hetero)cycloalkyl or (hetero)aryl group and at least one acid chemical function chosen in particular from carboxyl COOH, sulfuric $SO_3H$, $SO_2H$, and phosphoric $PO_3H_2$, $PO_4H_2$.

More particularly, the acids used are chosen from hydrochloric acid HCl, hydrobromic acid HBr, sulfuric acid $H_2SO_4$, alkylsulfonic acids: $(C_1$-$C_6)Alk$-$S(O)_2OH$ such as methylsulfonic acid and ethylsulfonic acid; arylsulfonic acids: Ar—$S(O)_2OH$ such as benzenesulfonic acid and toluenesulfonic acid; $(C_1$-$C_6)$alkoxysulfinic acids: Alk-O—S(O)OH such as methoxysulfinic acid and ethoxysulfinic acid; aryloxysulfinic acids such as tolueneoxysulfinic acid and phenoxysulfinic acid; phosphoric acid $H_3PO_4$; triflic acid $CF_3SO_3H$ and tetrafluoroboric acid $HBF_4$, and carboxylic acid(s) of formula (III) below:

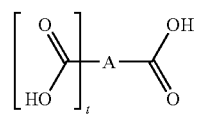

(II)

in which formula (II) or a salt thereof:

A represents a saturated or unsaturated, cyclic or non-cyclic and aromatic or non-aromatic hydrocarbon-based group, which is monovalent when t is 0 or polyvalent when t is greater than or equal to 1, comprising from 1 to 50 carbon atoms, which is optionally interrupted with one or more heteroatoms and/or optionally substituted, especially with one or more hydroxyl groups; preferably, A represents a monovalent $(C_1$-$C_6)$alkyl group or a polyvalent $(C_1$-$C_6)$ alkylene group optionally substituted with one or more hydroxyl groups.

Particularly, the carboxylic acids of formula (II) as defined above, and preferably the acid(s) used, is (are) an alpha-hydroxy acid such as lactic acid, glycolic acid, tartaric acid or citric acid.

The inorganic alkaline agent(s) are preferably chosen from aqueous ammonia, alkali metal carbonates or bicarbonates such as sodium or potassium carbonates and sodium or potassium bicarbonates, sodium hydroxide or potassium hydroxide, or mixtures thereof.

According to one advantageous embodiment of the invention, the alkaline agent(s) are organic amines, i.e. they contain at least one substituted or unsubstituted amino group.

The organic alkaline agent(s) are more preferentially chosen from organic amines with a $pK_b$ at 25° C. of less than 12, preferably of less than 10 and more advantageously still of less than 6. It should be noted that this is the $pK_b$ corresponding to the functional group having the highest basicity.

Hybrid compounds that may be mentioned include the salts of the amines mentioned previously with acids such as carbonic acid or hydrochloric acid.

The organic alkaline agent(s) are chosen, for example, from alkanolamines, oxyethylenated and/or oxypropylenated ethylenediamines, amino acids and the compounds having formula (III) below:

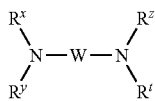

in which formula (III):
W is a divalent $C_1$-$C_6$ alkylene radical optionally substituted with a hydroxyl group or a $C_1$-$C_6$ alkyl radical, and/or optionally interrupted with one or more heteroatoms such as oxygen or NR";
$R^x$, $R^y$, $R^z$, $R^t$ and $R^u$, which are identical or different, represent a hydrogen atom or a $C_1$-$C_6$ alkyl, $C_1$-$C_6$ hydroxyalkyl or $C_1$-$C_6$ aminoalkyl radical.

Preferably, the alkanolamine is ethanolamine (or monoethanolamine).

In a variant of the invention, the composition comprises, as alkaline agent, one or more alkanolamines (preferably ethanolamine) and aqueous ammonia. In this variant, the alkanolamine(s) are present in a predominant amount relative to the aqueous ammonia.

More preferentially, the pH is adjusted so that the pH is between 2.5 and 9.5 inclusive, or between 1 and 6 inclusive, more particularly between 2 and 5 and preferably between 3 and 4, by means of $NH_4OH$ or citrate buffer.

The Process for Treating Keratin Fibres

The process for treating keratin fibres, in particular human keratin fibres such as the hair, employs ingredients a) and b) as defined above.

Process for treating keratin fibres, in particular the hair, comprising:
(i) a step consisting in applying, to said fibres, a) one or more, preferably nonionic or anionic, oxidized polysaccharide(s) as defined above; and
(ii) a step consisting in applying, to said fibres, b) one or more (poly)saccharide(s) with amine group(s) as defined above;

it being understood that steps (i) and (ii) may be carried out simultaneously or sequentially, and preferably steps (i) and (ii) are carried out simultaneously.

According to one particular embodiment of the process of the invention, steps (i) and (ii) are carried out simultaneously by applying, to the keratin fibres, a composition comprising a) one or more oxidized polysaccharide(s) as defined above, and b) one or more (poly)saccharide(s) with amine group(s) as defined above.

According to one particular embodiment of the invention, the process for treating keratin fibres comprises an additional step iii) of heating the keratin fibres, preferably to a temperature of at least 100° C., in particular to a temperature of between 100° C. and 250° C. inclusive. Preferably, the step of heating the keratin fibres is carried out at a temperature ranging from 150° C. to 220° C., preferably ranging from 160° C. to 220° C., preferentially ranging from 160° C. to 200° C., especially ranging from 170° C. to 190° C. It is understood that the heating temperatures are the temperatures of the heating means, in particular the iron plates when it is an iron, and not the temperature of the keratin fibres.

This heating step iii) is advantageously carried out using an iron.

The heating step makes it possible to optimize the effects of the process, and especially to optimize the persistence of the cosmetic properties after one or more shampooing washes.

For the purposes of the present invention, the term "iron" means a device for heating keratin fibres by placing said fibres and the heating device in contact with one another.

The end of the iron which comes into contact with the keratin fibres generally has two flat surfaces. These two surfaces may be made of metal or ceramic. In particular, these two surfaces may be smooth or crimped or curved.

The heating step may be carried out by means of a straightening iron, a curling iron, a crimping iron or a steam iron. Preferably, the heating step is carried out using a straightening iron.

As examples of irons that may be used in the heating process according to the invention, mention may be made of any type of flat iron, and in particular, in a nonlimiting manner, those described in patents U.S. Pat. Nos. 5,957,140 and 5,046,516.

The iron may be applied by successive separate strokes lasting a few seconds or by gradual movement or sliding along tresses of keratin fibres, especially of hair.

Preferably, the iron is applied in the process according to the invention by a continuous movement from the root to the end of the hair, in one or more passes, in particular in two to twenty passes. The duration of each pass of the iron may last from 2 seconds to 1 minute.

Preferably, the step of heating the keratin fibres is carried out for a time that may range from 2 seconds to 30 minutes, and preferentially from 2 seconds to 20 minutes, better still from 2 seconds to 10 minutes, better still from 2 seconds to 5 minutes and even better still from 2 seconds to 2 minutes.

The process according to the invention may also comprise an additional step of drying the keratin fibres after the application of the oxidized polysaccharide and/or of the (poly)saccharide(s) with amine group(s) or of the cosmetic composition(s) containing the same and before the step of heating the keratin fibres carried out at a temperature of at least 100° C. The drying step may be carried out using a hairdryer or a hood or by natural drying. The drying step is advantageously carried out at a temperature ranging from 20 to 70° C.

After the heating step, the keratin fibres may be optionally rinsed with water or washed with a shampoo. The keratin fibres are then optionally dried using a hairdryer or a hood or in the open air.

According to one embodiment, the process according to the invention is carried out on natural keratin fibres, especially natural hair.

According to another embodiment, the process according to the invention is carried out on damaged keratin fibres, especially damaged hair. As indicated previously, the term "damaged hair" means dry or coarse or brittle or split or limp hair.

According to another embodiment, the treatment process according to the invention is preferably carried out on sensitized keratin fibres, especially sensitized hair, such as bleached, artificially dyed, relaxed or permanent-waved fibres.

The process according to the invention may be carried out on keratin fibres, especially hair, which is dry or wet. Preferentially, the process is carried out on dry keratin fibres, especially dry hair.

The cosmetic composition(s) used according to the invention are advantageously applied to the keratin fibres in an amount ranging from 0.1 to 10 grams and preferably from 0.2 to 5 grams of composition per gram of keratin fibres.

After application of the cosmetic composition to the keratin fibres, the latter may be wrung out to remove the excess composition or washed with water or with a shampoo.

After application to the keratin fibres of the ingredient a) and/or the ingredient b) as defined above, or of a cosmetic composition containing the same, and before carrying out the step of heating the keratin fibres, the oxidized polysaccharide(s) and/or the (poly)saccharide(s) with amine group(s) as defined above or the composition(s) containing the same may be left on for a time ranging from 1 to 60 minutes, preferably ranging from 2 to 50 minutes and preferentially ranging from 5 to 45 minutes. The leave-on period may take place at a temperature ranging from 15° C. to 45° C., preferably at room temperature (25° C.).

According to one embodiment of the process according to the invention, the oxidized polysaccharide(s) a) as defined above and the (poly)saccharide(s) with amine group(s) b) as defined above are present in separate cosmetic compositions. They are therefore applied separately to the keratin fibres.

According to one particular embodiment of the process of the invention, the step of applying i) the oxidized polysaccharide(s) a) employs a composition comprising at least one oxidized polysaccharide as defined above, preferably in a content ranging from 0.05% to 15% by weight, preferably ranging from 0.1% to 10% by weight and more preferentially ranging from 0.2% to 6% by weight relative to the total weight of the composition.

According to one particular embodiment of the invention, the step of the process of applying ii) the (poly)saccharide(s) with amine group(s) b) employs a composition comprising at least one (poly)saccharide with amine group(s) as defined above in an amount of between 0.01% and 10% by weight relative to the total weight of the composition, more particularly of between 0.1% and 5% by weight relative to the total weight of the composition.

Particularly when b) is a monosaccharide with amine group(s) as defined above then it is in an amount of between 0.2% and 6% relative to the total weight of the composition.

Preferentially when b) is a polysaccharide with amine group(s) as defined above then it is in an amount of between 0.01% and 1.5%, more preferentially of between 0.1% and 1.1% by weight relative to the total weight of the composition.

According to another embodiment of the process according to the invention, the ingredients a) and b) as defined above are present in the same cosmetic composition.

They are therefore applied simultaneously to the keratin fibres. In this case, the preferred amounts are as follows:
For a) oxidized polysaccharide(s) as defined above, the specific amount is between 0.05% and 15% by weight, preferably between 0.1% and 10% by weight and more preferentially between 0.2% and 6% by weight relative to the total weight of the composition.
For b) (poly)saccharide(s) with amine group(s) as defined above, the specific amount is between 0.01% and 10% by weight relative to the total weight of the composition and more particularly between 0.1% and 5% by weight relative to the total weight of the composition. When b) is a polysaccharide with amine group(s) as defined above then it is in an amount of between 0.01% and 1.5%, more preferentially of between 0.1% and 1.1% by weight relative to the total weight of the composition.

According to a first embodiment of the process according to the invention, the following steps are carried out, in the following order: the step of applying the ingredient a) as defined above, then the step of applying the ingredient b) as defined above and then the heating step. Advantageously, the ingredient a) is present in a first cosmetic composition and the ingredient b) is present in a second cosmetic composition. This second composition is separate from the first composition.

According to a second embodiment of the process according to the invention, the following steps are carried out, in the following order: simultaneously, the step of applying the ingredient a) and the step of applying the ingredient b) and then the heating step. Advantageously, the ingredient a) and the ingredient b) are present in a single cosmetic composition.

According to a third embodiment of the process according to the invention, the following steps are carried out, in the following order: the step of applying the ingredient a), then the heating step, then the step of applying the ingredient b) and then optionally an additional heating step.

The treatment process according to the invention may be carried out before, during and/or after an additional process of cosmetic treatment of the keratin fibres, such as a process for temporarily shaping (shaping with curlers, a crimping iron or a straightening iron) or a process for durably shaping (permanent-waving or relaxing) the keratin fibres.

The treatment process may be carried out as a pre-treatment to a dyeing or relaxing process and/or a permanent-waving process so as to cosmetically protect the keratin fibres against these treatments. In other words, this process is carried out to preserve the cosmetic properties of the keratin fibres before a cosmetic treatment process as described previously.

In particular, the treatment process is performed as a post-treatment to a bleaching, artificial dyeing or relaxing process and/or a permanent-waving process so as to repair said fibres.

The process according to the invention may be carried out during a cosmetic treatment process so as to repair said fibres.

In particular, the treatment process according to the invention may be carried out on damaged keratin fibres.

In other words, the treatment process according to the invention is preferably carried out on sensitized keratin fibres such as bleached, dyed, relaxed or permanent-waved fibres.

In particular, the treatment process may be carried out before a bleaching, dyeing or relaxing process and/or a permanent-waving process on keratin fibres.

As a variant, the treatment process may be carried out during and/or after a cosmetic process for treating keratin fibres, in particular:
i) during and/or after a process for dyeing or a process for permanent-waving or a process for relaxing keratin fibres, and
ii) after a process for bleaching keratin fibres.

According to one embodiment, the treatment process according to the invention is carried out after a process for bleaching the keratin fibres.

Kit

Another subject of the invention is a multi-compartment kit or device comprising:
  a first cosmetic composition comprising a) at least one oxidized polysaccharide as defined above;
  a second cosmetic composition comprising b) at least one (poly)saccharide substituted with at least one amine group; and optionally, a device for heating the keratin fibres to a temperature of at least 100° C., preferably ranging from 100 to 250° C., the first and second compositions each being packaged in a separate packaging assembly.

The composition packaging assembly is, in a known manner, any packaging that is suitable for storing cosmetic compositions (especially a bottle, tube, spray bottle or aerosol bottle).

Such a kit allows the process for treating keratin fibres according to the invention to be carried out.

The examples that follow are given as illustrations of the present invention.

The amounts indicated in the examples are expressed as weight percentages.

EXAMPLES

The following compositions were prepared; the % are percentages by weight in g per 100 g of composition.

| Compositions | | Ingredients |
|---|---|---|
| Composition 1 | Control | Milli-Q water only |
| Composition 2 | Comparative | Oxidized inulin (OI)* at 5% in water, spontaneous pH of 3.0 |
| Composition 3 | Comparative | Glucosamine at 5% in water, spontaneous pH of 4.4 |
| Composition 4 | Invention | OI* at 5% + glucosamine at 5% in water, spontaneous pH of 3.0 |
| Composition 5 | Comparative | Polyglucosamine - chitosan** at 1% in water, spontaneous pH of 4.3 |
| Composition 6 | Invention | OI at 5% + polyglucosamine - chitosan** at 1% in water, spontaneous pH of 3.0 |

*Chitosan sold bySigma Aldrich under reference 523682.
**The oxidized inulin (OI) polymer was prepared by oxidation of inulin sold under the name Inutec N25 by Orafti, by performing a reactive extrusion process as described in the article "Water soluble oxidized starches by peroxide reactive extrusion" by R. E. Wing and J. L. Willett, Industrial Crops and Products 7, 1997, pages 45-52. A BC21 co-rotating twin-screw extruder sold by the company Clextral was used, and aqueous hydrogen peroxide solution was used as oxidizing agent.
OI: is obtained by reactive extrusion of a mixture of 78% by weight of inulin and 1.57% by weight of aqueous hydrogen peroxide solution; the spontaneous pH after reactive extrusion is 3.8. Compound 1 thus obtained has a carbonyl content of 1.23% (w/w) and a carboxyl content of 0.17% (w/w).

Evaluation Protocol

The tests for evaluating the treatment of the keratin fibres were carried out in the following way:

Straight, 20 cm, 1.3 g locks of caucasian hair were bleached (alkaline sensitivity AS 20%) and then underwent 10 cycles of exposure according to the following routine:
1) Placing the dry locks of hair in contact with a composition 1 to 5 in an amount of 2 g of composition per 1 g of hair, with 30 minutes of immersion at 40° C.;
2) Wringing out the locks then drying with a hair dryer at 60° C. with passage of a soft brush;
3) Applying a straightening iron at 190° C.: 5 passes of 9 seconds;
4) Wetting the locks with tap water, applying a shampoo containing 2% lauryl ether sulfate (% in g per 100 g composition), massaging for 15 seconds and careful rinsing with water at 37° C. for 10 seconds;
5) Drying with a hood at 60° C. for 10 minutes.

Persistence on shampooing: repetition of the sequence of steps 4 and 5 described above 9 times.

Evaluations

Feel: After applying and drying, the dry locks were evaluated sensorially on tactile criteria by 5 members of laboratory personnel who had been trained in the sensory evaluation of hair. Only the ends of the locks (bottom 3 cm) were evaluated. A score from 1 (locks very coarse to the touch) to 5 (locks very soft to the touch) was given. The averages of these scores are reported.

Disentangling: Tests of disentangling using a comb were carried out after immersion for 10 seconds in water, by 5 passes of a small-toothed plastic comb (7 teeth/cm, diameter of the teeth approx. 800 µm). A score from 1 (locks very difficult to disentangle) to 5 (locks very easy to disentangle) was given. The averages of these scores are reported.

Results:

Protocol 1: application of ingredient a) oxidized polysaccharide (oxidized inulin)+b) monosaccharide with amine group (glucosamine) applied together to keratin fibres, followed by a heat treatment using a straightening iron

| | Average score for softness of dry locks | |
|---|---|---|
| Compositions | after 1 shampoo wash | after 10 shampoo washes |
| Composition 1 | 3.1 | 3.1 |
| Composition 2 | 3.4 | 3.3 |
| Composition 3 | 3.6 | 3.4 |
| Composition 4 | 4.2 | 3.8 |

The locks treated with composition 4 according to the invention are perceived to be softer than the locks treated with the other, comparative, compositions, after 1 or even 10 shampoo washes.

Protocol 2: application of ingredient a) oxidized polysaccharide (oxidized inulin)+b) polysaccharide with amine groups (chitosan) applied together to keratin fibres, followed by a heat treatment using a straightening iron

| | Average score for softness of ends of dry locks | |
|---|---|---|
| Composition | after 1 shampoo wash | after 10 shampoo washes |
| Composition 1 | 2.3 | 2.2 |
| Composition 2 | 2.4 | 2.4 |
| Composition 5 | 3.0 | 2.6 |
| Composition 6 | 3.4 | 3.1 |

Protocol 2

| | Average score for ease of wet disentangling | |
|---|---|---|
| Composition | after 1 shampoo wash | after 10 shampoo washes |
| Composition 1 | 2.2 | 2.3 |
| Composition 2 | 1.9 | 2.1 |
| Composition 5 | 3.7 | 3.0 |
| Composition 6 | 4.1 | 3.3 |

The locks treated with composition 6 according to the invention are perceived to be softer at their dry ends and easier to disentangle using a comb when wet than the locks treated with the other compositions, after 1 or even 10 shampoo washes.

These results show that combining ingredients a) and b), especially a) oxidized inulin and b) glucosamine, leads to better sensory results than the ingredients a) or b) used individually, with improved dry softness, and that this effect persists up to 10 shampoo washes.

It was also observed that combining ingredients a) and b), especially a) oxidized inulin and b) polyglucosamine, improves the ease of wet disentangling perceived and the softness of dry ends, compared to those ingredients used individually. It was observed that this effect persists even after 10 shampoo washes.

The invention claimed is:

1. A method for conditioning keratin fibers, comprising:
   (i) applying to the keratin fibers a first composition comprising at least one oxidized inulin;
   (ii) applying to the keratin fibers a second composition comprising at least one polyglucosamine; and
   (iii) heating the keratin fibers;
   wherein step (iii) is carried out after steps (i) and (ii), and wherein the keratin fibers are not shampooed prior to step (iii).

2. The method according to claim 1, wherein (i) and (ii) are carried out simultaneously.

3. The method according to claim 1, wherein the at least one oxidized inulin is present in the first composition in an amount ranging from about 0.05% to about 15% by weight, relative to the total weight of the first composition.

4. The method according to claim 1, wherein the at least one polyglucosamine is present in the second composition in an amount ranging from about 0.01% to about 10% by weight, relative to the total weight of the second composition.

5. The method according to claim 1, wherein the pH of the second composition ranges from about 2.5 to about 9.5.

6. The method according to claim 1, wherein (i) and (ii) are carried out simultaneously by applying to the keratin fibers the first composition comprising the at least one oxidized inulin and the second composition comprising the at least one polyglucosamine.

7. The method according to claim 1, wherein the keratin fibers are heated to a temperature ranging from about 100° C. to about 250° C.

8. The method according to claim 1, wherein the steps are carried out in the following order:
   (i) applying the first composition comprising the at least one oxidized inulin;
   (ii) applying the second composition comprising the at least one polyglucosamine; and
   (iii) heating the keratin fibers to a temperature ranging from about 100° C. to about 250° C.

9. The method according to claim 1, wherein (i) and (ii) are carried out sequentially in any order.

* * * * *